United States Patent [19]

Emori et al.

[11] 4,087,458
[45] May 2, 1978

[54] PROCESS FOR PREPARATION OF 2-(AMYLBENZOYL)BENZOIC ACID

[75] Inventors: Fumitoshi Emori, Gojoh; Yasuhisa Iwasaki, Ikoma; Takao Yoshimura, Nara, all of Japan

[73] Assignee: Yamamoto Kagaku Gosei Co., Ltd., Yao, Japan

[21] Appl. No.: 794,620

[22] Filed: May 6, 1977

[30] Foreign Application Priority Data

May 10, 1976 Japan .................................. 51-53676
May 19, 1976 Japan .................................. 51-58042

[51] Int. Cl.² ............................................. C07C 65/20
[52] U.S. Cl. .................................... 260/517; 260/369; 423/588
[58] Field of Search .......................................... 260/517

[56] References Cited
U.S. PATENT DOCUMENTS 3,764,664  10/1973  Suda et al. ........................... 260/517

*Primary Examiner*—Jane S. Myers

*Attorney, Agent, or Firm*—Armstrong, Nikaido, Marmelstein & Kubovcik

[57] ABSTRACT

This invention relates to an improvement in the process for preparation of 2-(amylbenzoyl)benzoic acid containing a high percentage of 2-(t-amylbenzoyl)benzoic acid. More particularly it relates to a process for preparation of 2-(amylbenozyl)benzoic acid wherein said 2-(amylbenzoyl)benzoic acid is prepared by reacting t-amylbenzene with phthalic anhydride in the presence of Lewis acid, characterized by that 2-(amylbenzoyl)benzoic acid containing a high percentage of 2-(t-amylbenzoyl)benzoic acid is produced by suppressing the undesirable isomerization reaction of the amyl radical by applying one of the means selected from the group consisting of the means of introducing an inert gas into the reaction system and the means of reducing the pressure of the reaction system. 2-(Amylbenzoyl)benzoic acid is a compound useful as the starting material of preparation of 2-amylanthraquinone which is an effective organic catalyst in the manufacture of hydrogen peroxide.

8 Claims, No Drawings

PROCESS FOR PREPARATION OF 2-(AMYLBENZOYL)BENZOIC ACID

BACKGROUND OF THE INVENTION

Hydrogen peroxide has heretofore been manufactured by the electrolysis of ammonium hydrogensulfate solution, but recently a process for its manufacture using anthraquinone is being widely adopted. The process for manufacturing hydrogen peroxide using anthraquinone is what is called "anthraquinone process", in which as the working solution use is made of a solution obtained by dissolving an alkylanthraquinone in a suitable solvent or a mixture of solvents. In this process hydrogen peroxide is obtained in such a way that first hydrogen gas is blown into the working solution so as to reduce the alkylanthraquinone in the solution to alkylanthrahydroquinone, and then, into the resulting solution is blown an oxygen-containing gas to effect oxidation, whereby the alkylanthrahydroquinone is again oxidized to regenerate the alkylhydroquinone and at the same time hydrogen peroxide is generated. While the hydrogen peroxide thus produced is recovered by extraction with water from the working solution, the working solution is circulated for rense.

As the alkylanthraquinone used in the above described process there may be mentioned 2-ethylanthraquinone, 2-t-butylanthraquinone, 2-amylanthraquinone, etc., but among them 2-amylanthraquinone (hereinafter referred to as "AMQ") is the most useful compound because of its high solubility in the working solution.

Thus, the AMQ now used in the industry is always a mixture of 2-t-amylanthraquinone (hereinafter referred to as "t-AMQ") and 2-s-isoamylanthraquinone(- hereinafter referred to as "s-AMQ"), and such a situation indeed stems from the fact that the 2-(amylbenzoyl)benzoic acid itself which is the starting material of preparation of AMQ, is a mixture of 2-(t-amylbenzoyl)-benzoic acid (hereinafter sometimes referred to as "AMB acid") and 2-(s-isoamylbenzoyl)benzoic acid (hereinafter referred to as "s-AMB acid"). That is to say, in the process for preparation of AMB acid, wherein t-amylbenzene is reacted with phthalic anhydride in the presence of Lewis acid, it is impossible to obtain a mixture containing more than 55% of t-AMB acid, so that also in the AMQ prepared from such AMB acid the content of t-AMQ cannot be more than 55% as a natural consequence. This is because when t-amylbenzene and phthalic anhydride react in the presence of Lewis acid, portion of the t-amyl radical is converted to s-isoamyl radical by isomerization.

DESCRIPTION OF PRIOR ART

As described in Japanese Public Disclosure of Patent Application No. 75558/1973, in the case where hydrogen peroxide is manufactured by the use of a mixture of t-AMQ and s-AMQ, if s-AMQ is predominant in the mixture ratio, the solubility of amylanthrahydroquinone in the working solution decreases, so that not only does the yield of hydrogen peroxide per a definite quantity of working solution decrease, but also portion of AMQ suffers decomposition to form oxyanthrone, tetrahydroanthrone, anthrone, etc. which render the regeneration of AMQ impossible, at the same time causing a considerable difficulty in the pufication of hydrogen peroxide due to these impurities. Such being the case, in order to prepare AMQ containing a high percentage of t-AMQ a number of investigations have been attempted. For instance, there have been proposed (1) a process wherein t-AMQ is separated from the conventional mixture of t-AMQ and s-AMQ (Japanese Public Disclosure of Patent Application No. 75558/1973), (2) a process wherein t-amylmagnesium parahalide obtained by reacting p-halo-t-amylbenzene with magnesium is condensed with phthalic anhydride to give 2-(4'-t-amylbenzoyl)benzoic acid and then this is converted to t-AMQ by cyclization (Japanese Patent Publication No. 32517/1972 corresponding to French Patent No. 6917283), and (3) a process wherein AMB acid containing a high percentage of t-AMB acid is prepared by the use of both Lewis acid and phthalic anhydride in large excess to t-amylbenzene, and then this is converted to AMQ containing a high percentage of t-AMQ by cyclization (Japanese Public Disclosure of Patent Application No. 75558/1973). But, in the process of (1) the yield of t-AMQ decreases inevitably, and in the processes of (2) and (3) the adoption of Grignard process and the use of Lewis acid and phthalic anhydride in large excess add to the cost, and so on, so that it is the present situation that such deficiencies are hampering the industrial practice in any of these processes.

SUMMARY OF THE INVENTION

In view of such a situation the present inventors have made an elaborate investigation in order to obtain the AMB acid containing a high percentage of t-AMB acid which may be used as the starting material for the preparation of the AMQ containing a high percentage of t-AMQ. As a result it was discovered that when t-amylbenzene reacts with phthalic anhydride in the presence of Lewis acid, the AMB acid containing a high percentage of t-AMB acid can be obtained with extreme ease merely by applying one of the means selected from the group consisting of the means of introducing an inert gas or an inert low boiling liquid gasifiable at the reaction temperature into the reaction system and the means of reducing the pressure of the reaction system, and thus the present invention was achieved.

That is to say, in accordance with this invention the AMB acid containing a high percentage of t-AMB acid can be obtained by applying either the means of introducing an inert gas or an inert low boiling liquid gasifiable at the reaction temperature into the reaction system or the means of reducing the pressure of the reaction system under otherwise the same conditions as the conventional process, and using the AMB acid thus obtained as the starting material, the AMQ containing a high percentage of t-AMQ can be obtained by the conventional process.

The reason why the application of such means enables us to obtain the AMB acid containing a high percentage of t-AMB acid is not yet clear and now under investigation, but it may probably be attributable to the fact that the expulsion of the hydrogen halide formed as by-product during the reaction, resulting from the introduction of an inert gas or reduction of pressure, causes the concentration of said hydrogen halide within the reaction system to decrease, so that the isomerization of from t-amyl radical to s-amyl radical is hampered.

Either of the means of suppressing the isomerization, which are the indispensable requirement in the process of this invention, may achieve almost the same effect.

The process of this invention will be explained more fully below. The first means comprises an introduction of an inert gas or an inert low boiling liquid gasifiable at the reaction temperature into the reaction system while t-amyl benzene and phthalic anhydride are reacting.

As the inert gas use can be made of a variety of prior-known gases, such as, for instance, air, nitrogen, oxygen hydrogen, nitrogen oxide, sulfur dioxide, carbon monoxide, carbon dioxide, freon gas, sulfur hexafluoride, rare gases, e.g., helium, neon, argon, etc., and gaseous saturated hydrocarbons, e.g., methane, ethane, propane, etc. Among them the most preferable are air, oxygen, nitrogen, carbon dioxide, etc. As the inert low boiling liquid gasifiable at the reaction temperature use can be made of low boiling liquids such as, for instance, carbon disulfide, carbon tetrachloride, when the reaction is carried out at a temperature above the gasification temperature of said liquids.

There is no particular limitation to the method of introducing the above described gases or liquids. For instance, they may be either blown into the reaction mixture through a pipe, or blown against the surface of the reaction mixture under agitation, and so on. In such a case, however, it is preferable that the gas is introduced continuously or intermittently throughout the whole period of the reaction or in the initial stage of the reaction. The quantity of the gas introduced is not critical, but usually about 5–1500 cc per ml of reaction liquid will suffice.

The second method comprises reducing the pressure of the reaction system during the reaction. Since the reaction is usually conducted under the ordinary pressure, it will suffice to reduce the pressure of the reaction system somewhat below about 500 mm Hg. Although the extent of reduction of the pressure is not limitative, there is found a tendency that the larger the extent of reduction the more effect of this invention can be exhibited. Thus, it is usually preferable to carry out the reaction below 330 mm Hg. Even under a high vacuum as low as less than 10 mm Hg the process of this invention is of course feasible, but as the reaction solvent becomes more liable to volatilize it is economically undesirable. In this invention, therefore, it is most desirable to carry out the reaction under a pressure reduced to about 50–250 mm Hg. In the practice of this invention, there is no need of reducing the pressure of the reaction system throughout the whole period of the reaction, and by reducing the pressure of the reaction system only in the initial stage of the reaction the AMB acid containing a high percentage of t-AMB acid can be produced. The method of reducing the pressure of the reaction system is not critical, and use can be made of any usual pressure-reducing apparatuses such as a vacuum pump, an aspirator, etc. as they are.

The relative quantities of phthalic anhydride and t-amyl-benzene used in this invention are not particularly limitative, and the relative quantities within the range as used in the conventional process can always produce almost the same effect. Heretofore, it is also reported that by the use of an excess quantity of phthalic anhydride against the quantity of t-amyl-benzene the AMB acid containing a higher percentage of t-AMB acid can be prepared, but it is a quite surprising fact that when the process of this invention employs jointly this condition the percentage of t-AMB acid can be remarkably increased.

As the Lewis acid use can be made of a variety of prior-known compounds, such as aluminum chloride, aluminum bromide, ferric chloride, zinc chloride, boron trifluoride, etc., among which aluminum chloride is most preferable. The Lewis acid need not be used in large excess, so that as in the conventional process about 2 moles or excess (usually 2–2.2 moles) per mole of phthalic anhydride will suffice.

The solvents used in this invention include a variety of solvents usually used in Friedel-Crafts reaction, such as, for instance, chlorobenzene, dichlorobenzene, trichlorobenzene, tetrachloroethane, etc. The reaction temperature employed is usually 0°–100° C, or preferably 15°–60° C, and the reaction time is usually on the order of 2–15 hours.

The AMB acid prepared in the above described way is separated and purified by the prior-known conventional means such as recrystallization, etc.

The AMB acid containing a high percentage of t-AMB acid obtained in accordance with this invention can be readily converted to the AMQ containing a high percentage of t-AMQ.

DETAILED DESCRIPTION OF THE INVENTION

In order to make this invention more understandable Examples and comparative Examples will be shown below.

EXAMPLE 1

One mole of phthalic anhydride, 1.0 mole of t-amyl-benzene, and 2.1 moles of aluminum chloride are reacted for 4 hours at 40° C in 6.0 moles of chlorobenzene under a reduced pressure of 250 mm Hg. Then the reaction liquid is discharged into dilute sulfuric acid so as to decompose the reaction product, and the solvent layer is separated and thoroughly washed with hot water. After unreacted phthalic acid has bee removed, the AMB acid formed is extracted from the solvent layer with a dilute aqueous solution of sodium hydroxide. The extract obtained by the aqueous solution of sodium hydroxide is acidified with dilute sulfuric acid to deposit the AMB acid, which is filtered, thoroughly washed with water, and then dried to give a yield of 93 mole % as AMB acid. By the analysis of the AMB acid obtained based on NMR spectrum the ratio of the amyl radical isomers was found to be t-AMB acid : s-AMB acid = 65.3 : 34.7.

Further, when this AMB acid was cyclized with 2% fuming sulfuric acid according to the conventional process, AMQ could be readily obtained. By the analysis of this AMQ based on NMR spectrum the ratio of the isomers was found to be t-AMQ : s-AMQ = 68.5 : 31.5.

COMPARATIVE EXAMPLE 1

When Example 1 was repeated except that the reaction in Example 1 was carried out under the ordinary pressure, AMB acid was obtained in a yield of 90 mole %. Further, by its cyclization AMQ was obtained. The ratios of the isomers in the respective products were as follows:

t-AMB acid : s-AMB acid = 45.6 : 54.4,
t-AMQ : s-AMQ = 48.5 : 51.5.

EXAMPLE 2

By repeating Example 1 except that the reaction in Example 1 was carried out under a reduced pressure of 250 mm Hg for 2 hours after the initiation of the reaction, and after the pressure of the reaction system has been returned to the ordinary pressure the reaction was further continued for 2 hours, AMB was obtained (yield 90%). Further, by its cyclization AMQ was obtained.

The ratios of the isomers in the respective products were as follows:
t-AMB acid : s-AMB acid = 63.8 : 36.2,
t-AMQ : s-AMQ = 66.5 : 33.5.

EXAMPLE 3

By repeating Example 1 except that the reaction in Example 1 was carried out first by reducing the pressure within the reactor to about 50 mm Hg at the time of charging starting materials and then by maintaining the pressure at about 100 mm Hg., AMB was obtained (yield 95 mole %). By its cyclization AMQ was obtained. The ratios of the isomers in the respective products were as follows:
t-AMB acid : s-AMB acid = 71.3 : 28.7
t-AMQ : s-AMQ = 74.1 : 25.9

EXAMPLE 4

By repeating Example 1 except that chlorobenzene used in Example 1 was replaced by dichlorobenzene and the reaction was carried out at 50° C, there was obtained AMB acid, from which AMQ was obtained by cyclization. The ratios of the isomers in the respective products were as follows:
t-AMB acid : s-AMB acid = 71.6 : 28.4
t-AMQ : s-AMQ = 73.6 : 26.4

EXAMPLE 5

While blowing dry air into 6 moles of chlorobenzene liquid 1.0 mole of phthalic anhydride, 1.0 mole of t-amylbenzene, and 2.1 moles of aluminum chloride are added to the liquid. Continuing the blowing of dry air reaction is carried out for 4 hours at 40° C. Then the reaction liquid is poured in dilute sulfuric acid so as to decompose the reaction product, and the solvent layer is separated and, thoroughly washed with hot water. After removal of unreacted phthalic acid the AMB acid formed is extracted from said solvent layer with a dilute aqueous solution of sodium hydroxide. The extract obtained by the aqueous solution of sodium hydroxide is acidified with dilute sulfuric acid to deposit AMB acid, which is filtered, thoroughly washed with water, and then dried (yield 87 mole %). By the analysis of the AMB acid thus obtained based on NMR spectrum the ratio of the amyl radical isomers was found to be t-AMB acid : s-AMB acid = 77.6 : 22.4. Further, with respect to the AMQ which was obtained by cyclizing this AMB acid with fuming sulfuric acid, the analysis based on NMR spectrum showed t-AMQ : s-AMQ = 79.0 : 21.0 in the ratio of the isomers.

EXAMPLE 6

By repeating Example 5 except that dry air was blown against the surface of the reaction liquid instead of blowing dry air into the reaction liquid in Example 5, there was obtained AMB acid (yield 88 mole %), which was cyclized to give AMQ. The ratios of the isomers in the respective products were as follows:
t-AMB acid : s-AMB acid = 70.8 : 29.2
t-AMQ : s-AMQ = 73.7 : 26.3

EXAMPLE 7

By repeating Example 5 except that nitrogen was used in place of air and reaction was carried out for 2 hours at 55° C in Example 5, there was obtained AMB acid (yield 91 mole %), which was cyclized to give AMQ. The ratios of the isomers in the respective products were as follows:
t-AMB acid : s-AMB acid = 68.2 : 31.8
t-AMQ : s-AMQ = 71.7 : 28.3

EXAMPLE 8

By repeating Example 5 except that helium was used in place of air in Example 5, there was obtained AMB acid (yield 88 mole %). In this example, however, the helium was circulated for reuse. After the hydrogen chloride gas mixed in the gaseous effluent from the reaction system has been removed by the use of sodium hydroxide the gaseous effluent was again blown into the reaction mixture for reuse. The AMB acid was cyclized to give AMQ. The ratios of the isomers in the respective products were as follows:
t-AMB acid : s-AMB acid = 74.4 : 25.6
t-AMQ : s-AMQ = 75.9 : 24.1

EXAMPLE 9

By repeating Example 5 except that ordinary air as it was used in place of dry air in Example 5, there was obtained AMB acid (yield 72 mole %). In this example, however, air was allowed to enter the reaction system through an air introducing tube in such a way that placing one end of said air introducing tube outside the reaction system and the other end within the reaction liquid, the pressure of the reaction system is weakly reduced. The AMB acid was cyclized to give AMQ. The ratios of the isomers in the respective products were as follows:
t-AMB acid : s-AMB acid = 68.3 : 31.7,
t-AMQ : s-AMQ = 70.5 : 29.5.

EXAMPLE 10

By repeating Example 5 except that using 2.0 moles of aluminum chloride in Example 5 reaction was carried out for 10 hours at 30° C, there was obtained AMB acid (yield 85 mole %), which was cyclized to give AMQ. The ratios of the isomers in the respective products were as follows:
t-AMB acid : s-AMB acid = 85.1 : 14.9,
t-AMQ : s-AMQ = 87.3 : 12.7

EXAMPLE 11

By repeating Example 5 except that orthodichlorobenzene was used in place of chlorobenzene in Example 5 and reaction was carried out for 4 hours at 45° C, there was obtained AMB acid (yield 86 mole %), which was cyclized to give AMQ. The ratios of the isomers in the respective products were as follows:
t-AMB acid : s-AMB acid = 68.4 : 31.6,
t-AMQ : s-AMQ = 70.9 : 29.1

EXAMPLE 12

By repeating Example 5 except that the time of blowing dry air was limited to 2 hours after the initiation of the reaction, and thereafter, without blowing air, the reaction was further carried out for 2 hours, there was obtained AMB acid (yield 90 mole %), which was cyclized to give AMQ. The ratios of the isomers in the respective products were as follows:
t-AMB acid : s-AMB acid = 71.2 : 28.8,
t-AMQ : s-AMQ = 73.5 : 26.5.

EXAMPLE 13

While blowing dry air at a rate of 100 liters/hour into 12 moles of chlorobenzene liquid 2.0 moles of phthalic anhydride, 1.0 mole of t-amylbenzene, and 3.0 moles of aluminum chloride are added to the liquid. Continuing the blowing of dry air reaction is carried out for 2.0 hours at 40° C, and after stopping the blowing of air, the reaction is further continued for 2.0 hours at 40° C. Then the reaction liquid is poured in dilute sulfuric acid so as to decompose the reaction product. The resulting solution is allowed to stand overnight (several hours), and the crystals of phthalic acid deposited are removed by filtration. The solvent layer is separated from the filtrate and thoroughly washed with hot water to remove the remaining unreacted phthalic acid. Then AMB acid is extracted from the solvent layer with an aqueous solution of sodium hydroxide, and the extract obtained by the aqueous solution of sodium hydroxide is acidified with dilute sulfuric acid so as to deposit the AMB acid. The AMB acid thus deposited is recovered by filtration, thoroughly washed with water, and dried (yield 85 mole %). By the analysis of the AMB acid thus obtained based on NMR spectrum the ratio of the isomers of amyl radical was found to be t-AMB acid : s-AMB acid = 87.1 : 12.9. Further, with respect to the AMQ which was obtained by cyclizing this AMB acid with fuming sulfuric acid, the analysis based on NMR spectrum showed t-AMQ : s-AMQ = 89.0 : 11.0 in the ratio of the isomers.

COMPARATIVE EXAMPLE 2

By repeating Example 13 except that dry air is not blown in Example 13, AMB acid was obtained (yield 86 mole %). t-AMB acid : s-AMB acid = 61.0 : 39.0. The ratio of the isomers in the AMQ which was obtained by cyclizing this AMB acid according to the procedure in Example 13 was as follows:
t-AMQ : s-AMQ = 62.3 : 37.7.

EXAMPLE 14

By repeating Example 13 except that the reaction was carried out using the molar ratio of chlorobenzene: phthalic anhydride : t-amylbenzene : aluminum chloride = 6.0 : 1.0 : 1.0 : 2.0, there was obtained AMB acid (yield 87 mole %). t-AMB acid : s-AMB acid = 74.5 : 25.5; t-AMQ : s-AMQ = 75.8 : 24.2.

EXAMPLE 15

By repeating Example 13 except that the reaction was carried out using the molar ratio of chlorobenzene: phthalic anhydride : t-amylbenzene : aluminum chloride = 6.0 : 2.0 : 1.0 : 2.1, there was obtained AMB acid (yield 82 mole %). t-AMB acid : s-AMB acid = 89.2 : 10.8; t-AMQ : s-AMQ = 91.0 : 9.0.

When the reaction was carried out without air blowing the following result was obtained (yield of AMB acid 83 mole %). t-AMB acid : s-AMB acid = 63.8 : 36.2; t-AMQ : s-AMQ = 65.7 : 34.3.

EXAMPLE 16

By repeating Example 13 except that the reaction was carried out using the molar ratio of chlorobenzene : phthalic anhydride : t-amylbenzene : aluminum chloride = 6.0 : 1.5 : 1.0 : 2.1 and instead of blowing air the pressure of the reaction system was reduced to 100 mm Hg for the same period of time, there was obtained AMB acid (yield 84 mole %). t-AMB acid : s-AMB acid = 85.2 : 14.8; t-AMQ : s-AMQ = 86.6 : 13.4.

When the reaction was carried out under no reduction of pressure the following result was obtained (yield of AMB acid 82 mole %). t-AMB acid : s-AMB acid = 61.5 : 38.5; t-AMQ : s-AMQ = 65.7 : 34.3.

EXAMPLE 17

By repeating Example 13 except that the reaction was carried out at 30° C for 10 hours using the molar ratio of chlorobenzene : phthalic anhydride : t-amylbenzene : aluminum chloride = 6.0 : 2.5 : 1.0 : 2.1, while blowing nitrogen gas, there was obtained AMB acid (yield 51 mole %). t-AMB acid : s-AMB acid = 90.4 : 9.6; t-AMQ : s-AMQ = 92.3 : 7.6.

When the reaction was carried out without nitrogen gas blowing the following result was obtained (yield of AMB acid 49 mole %). t-AMB acid : s-AMB acid = 72.1 : 27.9; t-AMQ : s-AMQ = 73.8 : 26.2.

EXAMPLE 18

By repeating Example 13 except that the reaction was carried out using orthodichlorobenzene in place of chlorobenzene and in the molar ratio of orthodichlorobenzene : phthalic anhydride : t-amylbenzene : aluminum chloride = 20.0 : 5.0 : 1.0 : 6.6, there was obtained AMB acid (yield 84 mole %). t-AMB acid : s-AMB acid = 89.8 : 10.2; t-AMQ : s-AMQ = 91.5 : 8.5.

When the reaction was carried out without air blowing the following result was obtained (yield of AMB acid 86 mole %). t-AMB acid : s-AMB acid = 69.2 : 30.8; t-AMQ : s-AMQ = 70.1 : 29.9.

What is claimed:

1. A process for preparation of 2-(amylbenzoyl)benzoic acid containing 2-(t-amylbenzoyl)benzoic acid in a higher percentage than that of 2-(s-amylbenzoyl)benzoic acid, wherein said 2-(amylbenzoyl)benzoic acid is prepared by reacting t-amylbenzene with phthalic anhydride in the presence of Lewis acid, which process is characterized by that the isomerization reaction is suppressed by applying one of the means selected from the group consisting of the means of introducing an inert gas into the reaction system and the means of reducing the pressure of the reaction system.

2. The process as described in claim 1, wherein the isomerization reaction is suppressed by the means of introducing an inert gas into the reaction system.

3. The process as described in claim 2, wherein said inert gas or liquid is a gas or a mixture of gases selected from the group consisting of air, nitrogen, oxygen, carbon dioxide, carbon monoxide, freon, nitrogen oxide, sulfur dioxide, sulfur hexafluoride, rare gases, gaseous saturated hydrocarbons, and gasified low boiling liquids.

4. The process as described in claim 1, wherein said inert gas is a gas or a mixture of gases selected from the group consisting of air, oxygen, nitrogen, and carbon dioxide.

5. The process as described in claim 1, wherein the isomerization reaction is suppressed by the means of reducing the pressure of the reaction system.

6. The process as described in claim 5, wherein the pressure of the reaction system is reduced to less than 330 mm Hg.

7. The process as described in claim 5, wherein the pressure of the reaction system is reduced to 50–250 mm Hg.

8. A process for preparation of 2-(amylbenzoyl)benzoic acid containing 2-(t-amylbenzoyl)benzoic acid in a higher percentage than that of 2-(s-amylbenzoyl)benzoic acid, wherein said 2-(amylbenzoyl)benzoic acid is prepared by reacting t-amylbenzene with phthalic anhydride in the presence of Lewis acid, which process is characterized by that the t-amylbenzene and phthalic anhydride are reacted in a molar ratio of t-amylbenzene : phthalic anhydride larger than unity, while suppressing the isomerization reaction by applying one of the means selected from the group consisting of the means of introducing an inert gas into the reaction system and the means of reducing the pressure of the reaction system.

* * * * *

UNITED STATES PATENT AND TRADEMARK OFFICE
CERTIFICATE OF CORRECTION

PATENT NO. : 4,087,458
DATED : May 2, 1978
INVENTOR(S) : FUMITOSHI EMORI ET AL

It is certified that error appears in the above-identified patent and that said Letters Patent are hereby corrected as shown below:

Column 8, line 62, "larger than" should read --less than--.

Signed and Sealed this

Thirteenth Day of March 1979

[SEAL]

Attest:

RUTH C. MASON
*Attesting Officer*

DONALD W. BANNER
*Commissioner of Patents and Trademarks*